US010966871B2

(12) United States Patent
Lockwood et al.

(10) Patent No.: US 10,966,871 B2
(45) Date of Patent: *Apr. 6, 2021

(54) VACUUM BANDAGE PACKING (71) Applicant: KCI Licensing, Inc., San Antonio, TX (US)

(72) Inventors: Jeffrey S. Lockwood, Chesterfield, MO (US); Robert Petrosenko, Calgary, CA (US)

(73) Assignee: KCI Licensing, Inc., San Antonio, TX (US)

(*) Notice: Subject to any disclaimer, the term of this patent is extended or adjusted under 35 U.S.C. 154(b) by 597 days.

This patent is subject to a terminal disclaimer.

(21) Appl. No.: 15/814,203

(22) Filed: Nov. 15, 2017

(65) Prior Publication Data
US 2018/0071148 A1 Mar. 15, 2018

Related U.S. Application Data (63) Continuation of application No. 14/292,272, filed on May 30, 2014, now Pat. No. 9,844,471, which is a
(Continued)

(51) Int. Cl.
*A61F 13/00* (2006.01)
*A61F 13/02* (2006.01)
(Continued)

(52) U.S. Cl.
CPC .. *A61F 13/00068* (2013.01); *A61F 13/00063* (2013.01); *A61F 13/02* (2013.01);
(Continued)

(58) Field of Classification Search
CPC .......... A61F 13/00068; A61F 13/00021; A61F 13/00017; A61F 13/00029;
(Continued)

(56) References Cited

U.S. PATENT DOCUMENTS 1,355,846 A 10/1920 Rannells
2,547,758 A 4/1951 Keeling
(Continued)

FOREIGN PATENT DOCUMENTS

AU 550575 B2 3/1986
AU 745271 B2 3/2002
(Continued)

OTHER PUBLICATIONS

Louis C. Argenta, MD and Michael J. Morykwas, PHD; Vacuum-Assisted Closure: A New Method for Wound Control and Treatment: Clinical Experience; Annals of Plastic Surgery; vol. 38, No. 6, Jun. 1997; pp. 563-576.
(Continued)

*Primary Examiner* — Kim M Lewis (57) ABSTRACT

A vacuum bandage is provided for use with a wound having a wound surface. The bandage is connectable to a vacuum source and includes a wound dressing member having a wound contacting surface, a top surface, and a port configured for communication with the vacuum source. The wound dressing member further includes holes in the wound contacting surface configured for communication with the wound surface of the wound and a passageway between the port and each hole. The vacuum bandage further includes a pack adjacent to the top surface of the member. The pack may include an aperture positioned about the port.

9 Claims, 4 Drawing Sheets

Related U.S. Application Data continuation of application No. 13/709,161, filed on Dec. 10, 2012, now Pat. No. 8,884,094, which is a continuation of application No. 12/328,531, filed on Dec. 4, 2008, now Pat. No. 8,350,116, which is a continuation of application No. 10/495,908, filed as application No. PCT/US02/41229 on Dec. 20, 2002, now Pat. No. 7,534,927.

(60) Provisional application No. 60/344,589, filed on Dec. 26, 2001.

(51) Int. Cl.
 A61M 1/00 (2006.01)
 A61M 27/00 (2006.01)

(52) U.S. Cl.
 CPC ...... *A61F 13/0216* (2013.01); *A61F 13/0226* (2013.01); *A61M 1/0088* (2013.01); *A61M 27/00* (2013.01); *A61F 2013/0028* (2013.01); *A61F 2013/00536* (2013.01); *A61M 1/0056* (2013.01)

(58) Field of Classification Search
 CPC .......... A61F 13/00038; A61F 13/00063; A61F 13/00042; A61F 13/00046; A61F 13/02; A61F 13/0203; A61F 13/0206; A61M 1/0058; A61M 1/0066; A61M 1/008; A61M 1/0088
 See application file for complete search history.

(56) References Cited

U.S. PATENT DOCUMENTS

| | | |
|---|---|---|
| 2,632,443 A | 3/1953 | Lesher |
| 2,682,873 A | 7/1954 | Evans et al. |
| 2,910,763 A | 11/1959 | Lauterbach |
| 2,969,057 A | 1/1961 | Simmons |
| 3,066,672 A | 12/1962 | Crosby, Jr. et al. |
| 3,367,332 A | 2/1968 | Groves |
| 3,520,300 A | 7/1970 | Flower, Jr. |
| 3,568,675 A | 3/1971 | Harvey |
| 3,648,692 A | 3/1972 | Wheeler |
| 3,682,180 A | 8/1972 | McFarlane |
| 3,826,254 A | 7/1974 | Mellor |
| 4,080,970 A | 3/1978 | Miller |
| 4,096,853 A | 6/1978 | Weigand |
| 4,139,004 A | 2/1979 | Gonzalez, Jr. |
| 4,165,748 A | 8/1979 | Johnson |
| 4,184,510 A | 1/1980 | Murry et al. |
| 4,233,969 A | 11/1980 | Lock et al. |
| 4,245,630 A | 1/1981 | Lloyd et al. |
| 4,256,109 A | 3/1981 | Nichols |
| 4,261,363 A | 4/1981 | Russo |
| 4,275,721 A | 6/1981 | Olson |
| 4,284,079 A | 8/1981 | Adair |
| 4,297,995 A | 11/1981 | Golub |
| 4,333,468 A | 6/1982 | Geist |
| 4,373,519 A | 2/1983 | Errede et al. |
| 4,382,441 A | 5/1983 | Svedman |
| 4,392,853 A | 7/1983 | Muto |
| 4,392,858 A | 7/1983 | George et al. |
| 4,419,097 A | 12/1983 | Rowland |
| 4,465,485 A | 8/1984 | Kashmer et al. |
| 4,475,909 A | 10/1984 | Eisenberg |
| 4,480,638 A | 11/1984 | Schmid |
| 4,525,166 A | 6/1985 | Leclerc |
| 4,525,374 A | 6/1985 | Vaillancourt |
| 4,540,412 A | 9/1985 | Van Overloop |
| 4,543,100 A | 9/1985 | Brodsky |
| 4,548,202 A | 10/1985 | Duncan |
| 4,551,139 A | 11/1985 | Plaas et al. |
| 4,569,348 A | 2/1986 | Hasslinger |
| 4,605,399 A | 8/1986 | Weston et al. |
| 4,608,041 A | 8/1986 | Nielsen |
| 4,640,688 A | 2/1987 | Hauser |
| 4,655,754 A | 4/1987 | Richmond et al. |
| 4,664,662 A | 5/1987 | Webster |
| 4,710,165 A | 12/1987 | McNeil et al. |
| 4,733,659 A | 3/1988 | Edenbaum et al. |
| 4,743,232 A | 5/1988 | Kruger |
| 4,758,220 A | 7/1988 | Sundblom et al. |
| 4,787,888 A | 11/1988 | Fox |
| 4,826,494 A | 5/1989 | Richmond et al. |
| 4,838,883 A | 6/1989 | Matsuura |
| 4,840,187 A | 6/1989 | Brazier |
| 4,863,449 A | 9/1989 | Therriault et al. |
| 4,867,150 A | 9/1989 | Gilbert |
| 4,872,450 A | 10/1989 | Austad |
| 4,878,901 A | 11/1989 | Sachse |
| 4,897,081 A | 1/1990 | Poirier et al. |
| 4,906,233 A | 3/1990 | Moriuchi et al. |
| 4,906,240 A | 3/1990 | Reed et al. |
| 4,915,694 A | 4/1990 | Yamamoto et al. |
| 4,917,112 A | 4/1990 | Kalt |
| 4,919,654 A | 4/1990 | Kalt |
| 4,941,882 A | 7/1990 | Ward et al. |
| 4,953,565 A | 9/1990 | Tachibana et al. |
| 4,969,880 A | 11/1990 | Zamierowski |
| 4,985,019 A | 1/1991 | Michelson |
| 5,037,397 A | 8/1991 | Kalt et al. |
| 5,086,170 A | 2/1992 | Luheshi et al. |
| 5,092,858 A | 3/1992 | Benson et al. |
| 5,100,396 A | 3/1992 | Zamierowski |
| 5,134,994 A | 8/1992 | Say |
| 5,149,331 A | 9/1992 | Ferdman et al. |
| 5,167,613 A | 12/1992 | Karami et al. |
| 5,176,663 A | 1/1993 | Svedman et al. |
| 5,215,522 A | 6/1993 | Page et al. |
| 5,232,453 A | 8/1993 | Plass et al. |
| 5,261,893 A | 11/1993 | Zamierowski |
| 5,278,100 A | 1/1994 | Doan et al. |
| 5,279,550 A | 1/1994 | Habib et al. |
| 5,298,015 A | 3/1994 | Komatsuzaki et al. |
| 5,342,376 A | 8/1994 | Ruff |
| 5,344,415 A | 9/1994 | DeBusk et al. |
| 5,358,494 A | 10/1994 | Svedman |
| 5,437,622 A | 8/1995 | Carlon |
| 5,437,651 A | 8/1995 | Todd et al. |
| 5,447,492 A | 9/1995 | Cartmell et al. |
| 5,527,293 A | 6/1996 | Zamierowski |
| 5,549,584 A | 8/1996 | Gross |
| 5,556,375 A | 9/1996 | Ewall |
| 5,607,388 A | 3/1997 | Ewall |
| 5,636,643 A * | 6/1997 | Argenta ............ A61M 1/0088 128/897 |
| 5,645,081 A | 7/1997 | Argenta et al. |
| 6,033,390 A | 3/2000 | von Dyck |
| 6,071,267 A | 6/2000 | Zamierowski |
| 6,135,116 A | 10/2000 | Vogel et al. |
| 6,241,747 B1 | 6/2001 | Ruff |
| 6,287,316 B1 | 9/2001 | Agarwal et al. |
| 6,345,623 B1 | 2/2002 | Heaton et al. |
| 6,488,643 B1 | 12/2002 | Tumey et al. |
| 6,493,568 B1 | 12/2002 | Bell et al. |
| 6,553,998 B2 | 4/2003 | Heaton et al. |
| 6,685,681 B2 | 2/2004 | Lockwood et al. |
| 6,814,079 B2 | 11/2004 | Heaton et al. |
| 7,534,927 B2 | 5/2009 | Lockwood et al. |
| 7,846,141 B2 | 12/2010 | Weston |
| 8,062,273 B2 | 11/2011 | Weston |
| 8,216,198 B2 | 7/2012 | Heagle et al. |
| 8,251,979 B2 | 8/2012 | Malhi |
| 8,257,327 B2 | 9/2012 | Blott et al. |
| 8,350,116 B2 | 1/2013 | Lockwood et al. |
| 8,398,614 B2 | 3/2013 | Blott et al. |
| 8,449,509 B2 | 5/2013 | Weston |
| 8,529,548 B2 | 9/2013 | Blott et al. |
| 8,535,296 B2 | 9/2013 | Blott et al. |
| 8,551,060 B2 | 10/2013 | Schuessler et al. |
| 8,568,386 B2 | 10/2013 | Malhi |
| 8,679,081 B2 | 3/2014 | Heagle et al. |
| 8,834,451 B2 | 9/2014 | Blott et al. |

(56) References Cited

U.S. PATENT DOCUMENTS

| | | | |
|---|---|---|---|
| 8,884,094 B2 | 11/2014 | Lockwood et al. | |
| 8,926,592 B2 | 1/2015 | Blott et al. | |
| 9,017,302 B2 | 4/2015 | Vitaris et al. | |
| 9,198,801 B2 | 12/2015 | Weston | |
| 9,211,365 B2 | 12/2015 | Weston | |
| 9,289,542 B2 | 3/2016 | Blott et al. | |
| 2002/0065494 A1* | 5/2002 | Lockwood ........ | A61M 1/0088 604/313 |
| 2002/0077661 A1 | 6/2002 | Saadat | |
| 2002/0115951 A1 | 8/2002 | Norstrem et al. | |
| 2002/0120185 A1 | 8/2002 | Johnson | |
| 2002/0143286 A1 | 10/2002 | Tumey | |
| 2014/0163491 A1 | 6/2014 | Schuessler et al. | |
| 2015/0080788 A1 | 3/2015 | Blott et al. | |

FOREIGN PATENT DOCUMENTS

| | | |
|---|---|---|
| AU | 755496 B2 | 12/2002 |
| CA | 2005436 A1 | 6/1990 |
| DE | 26 40 413 A1 | 3/1978 |
| DE | 43 06 478 A1 | 9/1994 |
| DE | 29 504 378 U1 | 9/1995 |
| EP | 0100148 A1 | 2/1984 |
| EP | 0117632 A2 | 9/1984 |
| EP | 0161865 A2 | 11/1985 |
| EP | 0358302 A2 | 3/1990 |
| EP | 1018967 A1 | 7/2000 |
| GB | 692578 A | 6/1953 |
| GB | 2 195 255 A | 4/1988 |
| GB | 2 197 789 A | 6/1988 |
| GB | 2 220 357 A | 1/1990 |
| GB | 2 235 877 A | 3/1991 |
| GB | 2 329 127 A | 3/1999 |
| GB | 2 333 965 A | 8/1999 |
| JP | 4129536 B2 | 8/2008 |
| SG | 71559 | 4/2002 |
| WO | 80/02182 A1 | 10/1980 |
| WO | 87/04626 A1 | 8/1987 |
| WO | 90/010424 A1 | 9/1990 |
| WO | 93/009727 A1 | 5/1993 |
| WO | 94/020041 A1 | 9/1994 |
| WO | 96/05873 A1 | 2/1996 |
| WO | 97/18007 A1 | 5/1997 |
| WO | 99/13793 A1 | 3/1999 |

OTHER PUBLICATIONS

Susan Mendez-Eatmen, RN; "When wounds Won't Heal" RN Jan. 1998, vol. 61 (1); Medical Economics Company, Inc., Montvale, NJ, USA; pp. 20-24.

James H. Blackburn II, MD et al.: Negative-Pressure Dressings as a Bolster for Skin Grafts; Annals of Plastic Surgery, vol. 40, No. 5, May 1998, pp. 453-457; Lippincott Williams & Wilkins, Inc., Philidelphia, PA, USA.

John Masters; "Reliable, Inexpensive and Simple Suction Dressings"; Letter to the Editor, British Journal of Plastic Surgery, 1998, vol. 51 (3), p. 267; Elsevier Science/The British Association of Plastic Surgeons, UK.

S.E. Greer, et al. "The Use of Subatmospheric Pressure Dressing Therapy to Close Lymphocutaneous Fistulas of the Groin" British Journal of Plastic Surgery (2000), 53, pp. 484-487.

George V. Letsou, MD., et al; "Stimulation of Adenylate Cyclase Activity in Cultured Endothelial Cells Subjected to Cyclic Stretch"; Journal of Cardiovascular Surgery, 31, 1990, pp. 634-639.

Orringer, Jay, et al; "Management of Wounds in Patients with Complex Enterocutaneous Fistulas"; Surgery, Gynecology & Obstetrics, Jul. 1987, vol. 165, pp. 79-80.

International Search Report for PCT International Application PCT/GB95/01983; dated Nov. 23, 1995.

PCT International Search Report for PCT International Application PCT/GB98/02713; dated Jan. 8, 1999.

PCT Written Opinion; PCT International Application PCT/GB98/02713; dated Jun. 8, 1999.

PCT International Examination and Search Report, PCT International Application PCT/GB96/02802; dated Jan. 15, 1998 & dated Apr. 29, 1997.

PCT Written Opinion, PCT International Application PCT/GB96/02802; dated Sep. 3, 1997.

Dattilo, Philip P., JR., et al; "Medical Textiles: Application of an Absorbable Barbed Bi-directional Surgical Suture"; Journal of Textile and Apparel, Technology and Management, vol. 2, Issue 2, Spring 2002, pp. 1-5.

Kostyuchenok, B.M., et al; "Vacuum Treatment in the Surgical Management of Purulent Wounds"; Vestnik Khirurgi, Sep. 1986, pp. 18-21 and 6 page English translation thereof.

Davydov, Yu. A., et al; "Vacuum Therapy in the Treatment of Purulent Lactation Mastitis"; Vestnik Khirurgi, May 14, 1986, pp. 66-70, and 9 page English translation thereof.

Yusupov. Yu.N., et al; "Active Wound Drainage", Vestnki Khirurgi, vol. 138, Issue 4, 1987, and 7 page English translation thereof.

Davydov, Yu.A., et al; "Bacteriological and Cytological Assessment of Vacuum Therapy for Purulent Wounds"; Vestnik Khirugi, Oct. 1988, pp. 48-52, and 8 page English translation thereof.

Davydov, Yu.A., et al; "Concepts for the Clinical-Biological Management of the Wound Process in the Treatment of Purulent Wounds by Means of Vacuum Therapy"; Vestnik Khirurgi, Jul. 7, 1980, pp. 132-136, and 8 page English translation thereof.

Chariker, Mark E, M.D., et al; "Effective Management of incisional and cutaneous fistulae with closed suction wound drainage"; Contemporary Surgery, vol. 34, Jun. 1989, pp. 59-63.

Egnell Minor, Instruction Book, First Edition, 300 7502, Feb. 1975, pp. 24.

Egnell Minor: Addition to the Users Manual Concerning Overflow Protection—Concerns all Egnell Pumps, Feb. 3, 1983, pp. 2.

Svedman, P.: "Irrigation Treatment of Leg Ulcers", The Lancet, Sep. 3, 1983, pp. 532-534.

Chinn, Steven D. et al.: "Closed Wound Suction Drainage", The Journal of Foot Surgery, vol. 24, No. 1, 1985, pp. 76-81.

Arnljots, Björn et al.: "Irrigation Treatment in Split-Thickness Skin Grafting of Intractable Leg Ulcers", Scand J. Plast Reconstr. Surg., No. 19, 1985, pp. 211-213.

Svedman, P.: "A Dressing Allowing Continuous Treatment of a Biosurface", IRCS Medical Science: Biomedical Technology, Clinical Medicine, Surgery and Transplantation, vol. 7, 1979, p. 221.

Svedman, P. et al: "A Dressing System Providing Fluid Supply and Suction Drainage Used for Continuous of Intermittent Irrigation", Annals of Plastic Surgery, vol. 17, No. 2, Aug. 1986, pp. 125-133.

N.A. Bagautdinov, "Variant of External Vacuum Aspiration in the Treatment of Purulent Diseases of Soft Tissues," Current Problems in Modern Clinical Surgery: Interdepartmental Collection, edited by V. Ye Volkov et al. (Chuvashia State University, Cheboksary, U.S.S.R. 1986); pp. 94-96 (copy and certified translation).

K.F. Jeter, T.E. Tintle, and M. Chariker, "Managing Draining Wounds and Fistulae: New and Established Methods," Chronic Wound Care, edited by D. Krasner (Health Management Publications, Inc., King of Prussia, PA 1990), pp. 240-246.

G. Živadinovi?, V. ?uki?, Ž. Maksimovi?, ?. Radak, and P. Peška, "Vacuum Therapy in the Treatment of Peripheral Blood Vessels," Timok Medical Journal 11 (1986), pp. 161-164 (copy and certified translation).

F.E. Johnson, "An Improved Technique for Skin Graft Placement Using a Suction Drain," Surgery, Gynecology, and Obstetrics 159 (1984), pp. 584-585.

A.A. Safronov, Dissertation Abstract, Vacuum Therapy of Trophic Ulcers of the Lower Leg with Simultaneous Autoplasty of the Skin (Central Scientific Research Institute of Traumatology and Orthopedics, Moscow, U.S.S.R. 1967) (copy and certified translation).

M. Schein, R. Saadia, J.R. Jamieson, and G.A.G. Decker, "The 'Sandwich Technique' in the Management of the Open Abdomen," British Journal of Surgery 73 (1986), pp. 369-370.

D.E. Tribble, An Improved Sump Drain-Irrigation Device of Simple Construction, Archives of Surgery 105 (1972) pp. 511-513.

M.J. Morykwas, L.C. Argenta, E.I. Shelton-Brown, and W. McGuirt, "Vacuum-Assisted Closure: A New Method for Wound Control and (56) References Cited

OTHER PUBLICATIONS

Treatment: Animal Studies and Basic Foundation," Annals of Plastic Surgery 38 (1997), pp. 553-562 (Morykwas I).
C.E. Tennants, "The Use of Hypermia in the Postoperative Treatment of Lesions of the Extremities and Thorax," Journal of the American Medical Association 64 (1915), pp. 1548-1549.
Selections from W. Meyer and V. Schmieden, Bier's Hyperemic Treatment in Surgery, Medicine, and the Specialties: A Manual of Its Practical Application, (W.B. Saunders Co., Philadelphia, PA 1909), pp. 17-25, 44-64, 90-96, 167-170, and 210-211.
V.A. Solovev et al., Guidelines, The Method of Treatment of Immature External Fistulas in the Upper Gastrointestinal Tract, editor-in-chief Prov. V.I. Parahonyak (S.M. Kirov Gorky State Medical Institute, Gorky, U.S.S.R. 1987) ("Solovev Guidelines").
V.A. Kuznetsov & N.a. Bagautdinov, "Vacuum and Vacuum-Sorption Treatment of Open Septic Wounds," in II All-Union Conference on Wounds and Wound Infections: Presentation Abstracts, edited by B.M. Kostyuchenok et al. (Moscow, U.S.S.R. Oct. 28-29, 1986) pp. 91-92 ("Bagautdinov II").
V.A. Solovev, Dissertation Abstract, Treatment and Prevention of Suture Failures after Gastric Resection (S.M. Kirov Gorky State Medical Institute, Gorky, U.S.S.R. 1988) ("Solovev Abstract").
V.A.C. ® Therapy Clinical Guidelines: A Reference Source for Clinicians; Jul. 2007.

* cited by examiner

VACUUM BANDAGE PACKING

This application is a Continuation of U.S. patent application Ser. No. 14/292,272 filed on May 30, 2014, which is a Continuation of U.S. patent application Ser. No. 13/709,161 filed Dec. 10, 2012, now U.S. Pat. No. 8,884,094, issued Nov. 11, 2014, which is a Continuation of U.S. patent application Ser. No. 12/328,531 filed Dec. 4, 2008, now U.S. Pat. No. 8,350,116, issued Jan. 8, 2013, which is a Continuation of U.S. patent application Ser. No. 10/495,908 filed May 19, 2004, now U.S. Pat. No. 7,534,927, issued May 19, 2009, which is a U.S. national counterpart application of International Application Serial No. PCT/US02/041229 filed Dec. 20, 2002, which claims the benefit of U.S. Provisional Application Ser. No. 60/344,589 filed Dec. 26, 2001, the disclosures of each of which are expressly incorporated by reference herein.

BACKGROUND OF THE INVENTION

The present disclosure relates to packing for placement over a chronic wound, and particularly to packing for use with a vacuum bandage coupled to a vacuum source.

Gauze or commercially available foam packing is typically used to pack a wound. One example is the ALLEVYN® Cavity Wound Dressing available from Smith & Nephew. This particular wound dressing is made of a polyurethane foam. Gauze is often used to absorb liquid and exudate present on the wound surface.

SUMMARY OF THE INVENTION

The present invention comprises one or more of the following features or combinations thereof:

A bandage for use with a wound and a vacuum source is provided. The bandage comprises a wound dressing member having a wound contacting surface and a port configured for communication with the vacuum source. The member further includes holes formed in the wound contacting surface and configured for communication with a wound surface of the wound. The member includes a passageway between the port and each hole. The combination may further include a pack coupled to the top surface of the member. The pack may illustratively include an aperture positioned about the port of the member. A connecter of the member may be received within the aperture.

In illustrative embodiments, the pack further includes a bottom surface, a top surface, a side wall extending from the top surface to the bottom surface, and a slit in communication with the aperture. The slit is defined by first and second confronting interior surfaces which each extend from the top surface of the pack to the bottom surface and from the aperture to the side wall. The illustrative pack further includes an adhesive layer coupled to the bottom surface of the pack for coupling the pack to the top surface of the member. The pack may be made of either open-celled or closed-cell foam.

The member may be generally non-compressible and made of a medical grade silicone. The member may further include a connecter coupled to the top surface of the member. Such a connecter may be received within the aperture of the pack and configured for communication with the port of the member and the vacuum source.

Other features of the disclosure will become apparent to those skilled in the art upon consideration of the following detailed description of the preferred embodiments exemplifying the best mode of carrying out the disclosure as presently perceived.

BRIEF DESCRIPTION OF THE DRAWINGS

The detailed description particularly refers to the accompanying figures in which.

DETAILED DESCRIPTION OF THE DRAWINGS

Figure 1:
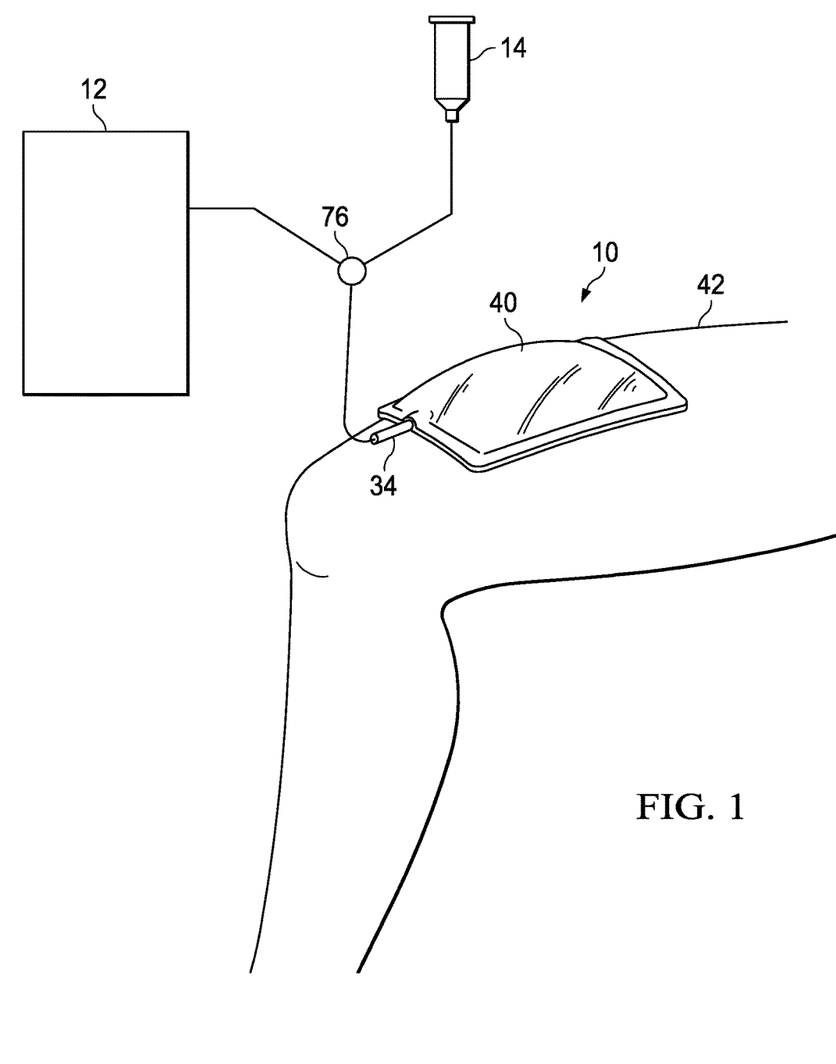
FIG. 1 is a part perspective, part diagrammatic view of a wound care bandage showing the wound care bandage located on the leg of a patient and coupled to both a vacuum and an irrigation source through the use of a switch valve.

A wound care bandage 10 is provided for use with a vacuum and irrigation source 12, 14, respectively, as shown in FIG. 1. An illustrative vacuum and irrigation source 12, 14 is disclosed in U.S. Patent Publication No. US 2002/0161317 A1 and U.S. Pat. No. 6,458,109, both of which are owned by the assignee of the present application and both of which are hereby incorporated herein by reference.

Figure 2:
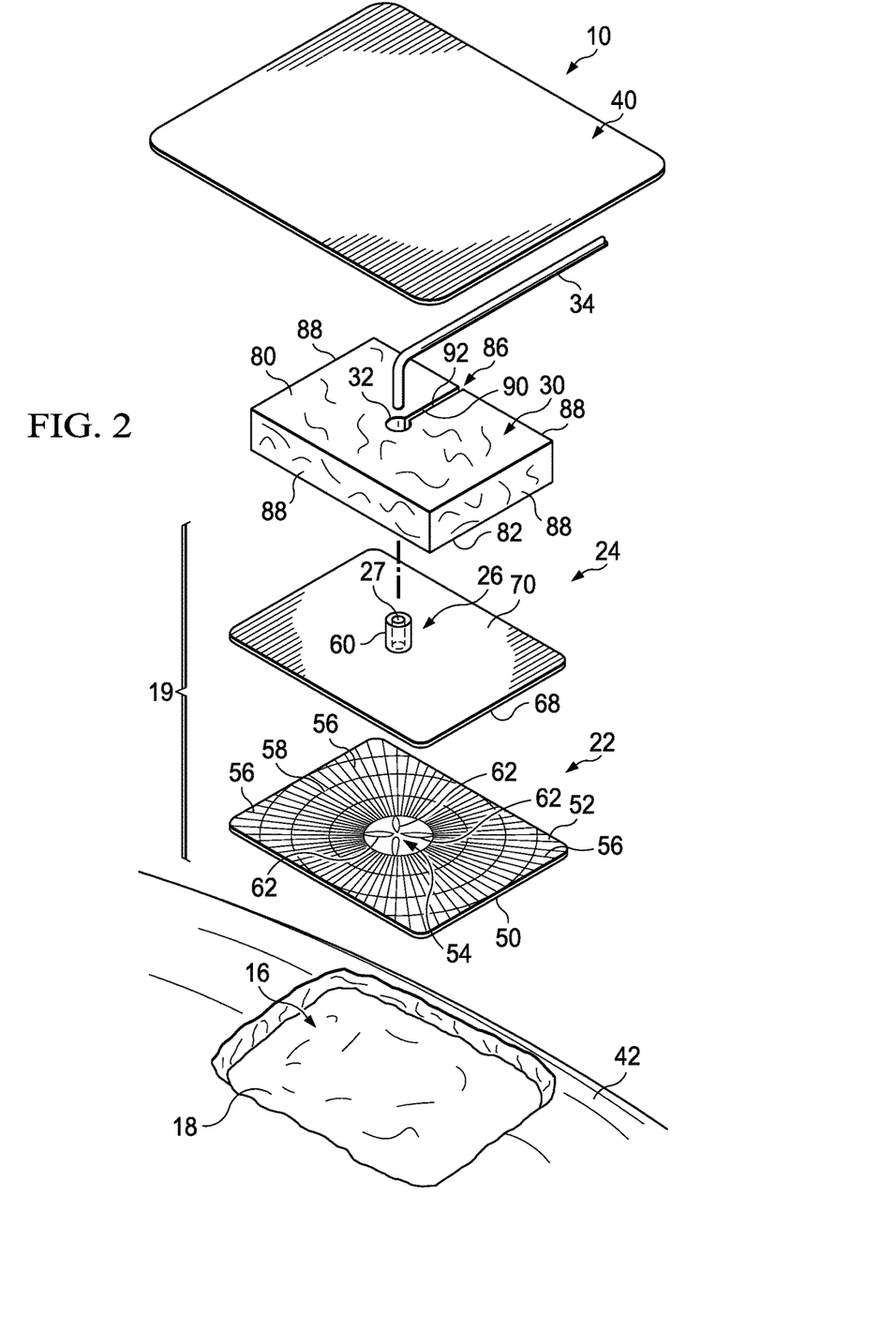
FIG. 2 is an exploded perspective view of the wound care bandage of FIG. 1 showing the bandage positioned above a wound bed and including a wound contacting layer and a cover which cooperate to form a wound dressing member for placement within the wound bed, and also showing a foam packing for placement adjacent the cover and a sealing film to cover the foam packing and member to seal about the wound.

Bandage 10 promotes the healing of a large wound 16 (shown in FIG. 2) by providing vacuum therapy to the wound 16 to promote blood flow and remove exudate from a wound surface 18 of the wound and by providing for irrigation of the wound 16 with fluids such as saline, for example. As shown in FIG. 2, wound care bandage 10 comprises a thin, flexible wound dressing member 19. Illustrative wound dressing members are disclosed in U.S. Patent Publication No. US 2002/0082567 A1, which is owned by the assignee of this present application and which is hereby incorporated herein by reference.

Figure 4:
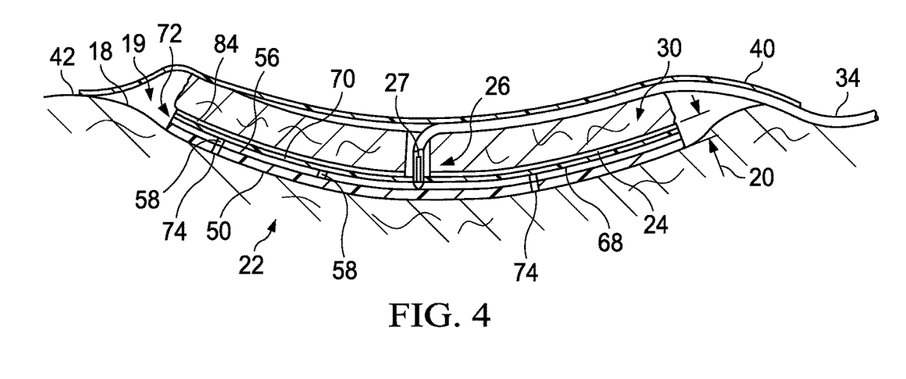
FIG. 4 is a sectional view of the bandage showing the member adjacent the wound, the packing adjacent the cover of the member, and a vacuum tube received within the aperture of the packing for coupling with the cover of the member, and further showing the sealing film positioned over the packing and tube to seal to the patient's healthy skin about the wound.

Bandage 10 also includes a foam packing 30 above and adjacent member 19, as shown in FIGS. 2 and 4. Packing 30 rests on member 19 and includes an aperture 32 for receiving a vacuum tube 34. As shown in FIG. 4, one end of vacuum tube 34 is coupled to member 19 and, as shown in FIG. 1, the other end of tube 34 is coupled to vacuum source 12 and/or irrigation source 14. Bandage 10 further includes a film 40 that is placed over member 19, packing 30, and tube 34 and that attaches to a patient's healthy skin 42 around wound 16. Packing 30 occupies a space between film 40 of bandage 10 and member 19.

Member 19, of bandage 10, is made of a medical grade silicone or other type of elastomer which is pliable. Two companies, for example, which manufacture such medical grade silicone are GE Silicones and NuSil Technology. It is within the scope of this disclosure, however, to include a wound dressing member made of any type of thin, flexible material that is non-porous and non-foam-like. This thin, flexible material is also generally non-absorptive. For example, materials such as polyvinylchloride (PVC), PVC free of diethylhexylphthalate (DEHP-free PVC), polyurethane, or polyethylene may be used in the manufacture of member 19.

Further, member 19 may be molded to include antimicrobial constituents. For example, it is within the scope if this disclosure to impregnate member 19 with silver ions which are known anti-microbials. Member 19 is also made of a generally non-adhesive material. Therefore, member 19 does not adhere to the wound surface 18. Further, member 19 is solid in nature and generally non-compressible. For example, when a negative pressure is applied to member 19, a thickness 20 of member 19, as shown in FIG. 4, remains relatively constant. Further, member 19 is generally transparent to enable a caregiver to be able to see the wound 16 through member 19 when member 19 is placed adjacent to wound surface 18. This transparency allows the caregiver to view the progress of the healing of the wound 16. Although packing 30 is placed over member 19, thus preventing a caregiver from viewing the wound surface 18, packing 30 is removable and replaceable without the need to remove member 19 from wound surface 18, as is described below. Therefore, the progress of the healing of wound 16 is viewable through member 19 when the caregiver is has removed packing 30 from member 19 to replace with a new packing 30.

As shown in FIG. 2, wound dressing member 19 is illustratively rectangular in shape. However, it is within the scope of this disclosure for member 19 to be any suitable shape. Further, member 19 may be cut to fit any size wound 16. Member 19 includes the combination of a wound contacting layer 22 and a cover 24. Member 19 also includes a connecter 26 coupled to cover 24 for communication with vacuum source 12 and/or irrigation source 14. It is also within the scope of this disclosure for connecter 26 to be formed integrally with cover 24 or to be a separate piece that is attached to cover 24.

Layer 22 includes a wound contacting surface 50 and an upper or opposite surface 52. Wound contacting surface 50, or portions thereof, contacts and generally conforms to the wound surface 18. Opposite surface 52 includes a central area 54 and a plurality of channels 56 which extend radially away from central area 54, as shown in FIG. 2. Central area 54 is recessed relative to the portions of upper surface 52 between channels 56. As shown in FIGS. 2 and 4, channels 56 are open at the sides and ends of member 19. Opposite surface 52 further includes concentric channels 58. Central area 54 is provided to communicate with vacuum source 12 and irrigation source 14 through a port 60 of cover 24, as described below.

A plurality of radially extending protrusions or bosses 62 are positioned around central area 54. Bosses 62 are positioned between central area 54 and channels 56, 58, as shown in FIG. 2. Bosses 62 prevent central area 54 from collapsing in on port 60 of cover 24 and forming an unwanted seal which would effectively block air flow through port 60 while suction is applied to bandage 10. Port 60 communicates with the vacuum source 12 and/or the irrigation source 14 via connecter 26 and tube 34, as shown in FIG. 2. As mentioned above, port 60 is in communication with central area 54 of layer 22.

Illustratively, four bosses 62 are shown in FIG. 2. However, it is within the scope of this disclosure to provide any number of bosses 62 or the like about central area 54 of layer 22 to prevent central area 54 from sealing off port 60 of cover 24 as suction is applied to bandage 10. Further, it is within the scope of this disclosure to include a boss or bosses 62 having any shape that prevents central area 54 from sealing off port 60 when suction is applied to bandage 10.

Connecter 26, as shown in FIGS. 2 and 4, is a tubal port coupled to a top surface 70 of cover 24 and in communication with port 60 of cover 24. As mentioned before, it is within the scope of this disclosure for connecter 26 to be a separate component of member 19 which is coupled to cover 24 or for connecter 26 to be molded integrally with cover 24. Connecter 26 includes a vertical passageway 27. Connecter 26 connects with tube 34 to provide a vertical tube attachment with respect to port 60. Vertical connector 26 is received within aperture 32 of packing 30. As mentioned above, however, it is within the scope of this disclosure to include a member 19 having only layer 22 and cover 24, without a connecter 26, for example. In such an example, tube 34 couples directly to cover 24 for direct communication with port 60. Cover 24 includes a bottom surface 68 and top surface 70, as shown in FIG. 2. Bottom surface 68 engages opposite surface 52 of layer 22, as shown in FIG. 4.

In some embodiments, member 19 is made by heat sealing opposite surface 52 of layer 22 and bottom surface 68 of cover 24 together and by heat sealing connecter 26 to top surface 70 of cover 24. Each of connecter 26, cover 24 (or the combination of cover 24 and connecter 26), and layer 22 may be pre-shaped and formed from semi-cured silicone. Once the connecter 26, cover 24, and layer 22 are placed together appropriately, the entire member 19 may be heated to heat seal and cure each of the three components to one another. Alternatively, for example, the cover 24 only may be made from semi-cured silicone while the connecter 26 and layer 22 may be made from fully cured silicone. Once placed together and heated, connecter 26 and layer 22 will heat seal to cover 24. Semi-cured silicone may be bought and pre-molded from a manufacturer such as NuSil Technology, for example. Although the method of heat sealing the cover 24, connecter 26, and layer 22 to each other is disclosed, it is within the scope of this disclosure to form member 19 by coupling layer 22, cover 24, and connector 26 together by another suitable means such as through the use of adhesives, for example. Further, it is within the scope of this disclosure to provide a member 19 where cover 24 lies adjacent to, but is not coupled to, layer 22.

As mentioned above, cover 24 is coupled to layer 22 and connecter 26 is coupled to cover 24 to form member 19. Cover 24 and layer 22 cooperate to form distinct passageways 72 of member 19 (as shown in FIG. 4) which are defined by channels 56, 58 of layer 22 and bottom surface 68 of cover 24. Passageways 72 are in communication with central area 54 of layer 22 and central area 64 of layer 22 is in communication with port 60 of cover 24 which is in communication with the vacuum and/or irrigation sources 12, 14 via connecter 26 and tube 34. Therefore, passageways 72 are in communication with the vacuum and/or irrigation sources 12, 14.

Layer 22 includes through holes 74 which extend from channels 56, 58 through layer 22 to wound contacting surface 50, as shown in FIG. 4. Holes 74 are distinct and are provided to communicate with channels 56, 58 of layer 22. Holes 74 therefore communicate with passageways 72 of member 19 and the vacuum and/or irrigation sources 12, 14 as well to allow the suction from the vacuum source 12 and/or the fluid from the irrigation source 14 to reach the wound surface 18 via the holes 74. Illustratively, holes 74 are 0.020 inch (0.508 mm) in diameter and are spaced approximately 0.500 inch (12.700 mm) apart along channels 56, 58 of layer 22. It is, however, within the scope of the disclosure to include holes having other suitable sized diameters and/or other suitable spacing that allow for the removal of exudate without clogging.

Illustrative member 19 of bandage 10 includes a smooth wound contacting surface 50, as shown in FIG. 2. Wound contacting surface 50 may also be ribbed, textured, or roughened. By providing member 19 with a ribbed, textured, or roughened surface, a space is created between surface 50 of layer 22 and wound surface 18. Through holes 74 communicate with this space which permits vacuum source 12 to establish a generally uniformly distributed vacuum or negative pressure to the wound surface 18 to draw blood from the body to the wound surface 18 and to draw exudate from the wound 16 through holes 74, into channels 56, 58 and passageways 72, and out port 60 of cover 24. It is within the scope of this disclosure to include other means for providing a space between surface 50 and wound surface 18 such as providing ribs, protrusions, channels, spacers, etc.

The vacuum or negative pressure which draws blood from the body to the wound surface 18 and draws exudate from the wound 16 up through member 19 promotes the healing of wound 16. As wound 16 heals, granulations form along the wound surface 18. Granulations, therefore, are the replacement within the wound bed of tissue lost. As the granulations fill in the wound bed causing the wound 16 to heal, member 19 rides up on the wound surface 18 on top of the granulations which are formed.

Although illustrative bandage 10 includes one central port 60, it is within the scope of this disclosure to include multiple ports. In order to accommodate different sized wounds 16, member 19 may be trimmed to fit a particular wound 16. Further, some embodiments of member 19 include scale markings. Scale markings indicate areas where a caregiver may trim member 19 to fit a particular wound 16. Further, the scale markings may denote measurement sizes, for example, to permit a caregiver to cut the member 19 to fit a pre-measured wound 16. In order to accommodate various types and placements of wounds on patients, it is within the scope of this disclosure to include a member or members in various conforming shapes and sizes suitable for treating chronic wounds on a patient's heel, abdomen, or sternum, for example.

A switch valve 76 is illustratively provided, as shown in FIG. 1, to allow a user to switch between the use of the vacuum source 12 and the irrigation source 14. It will be appreciated that a mechanism other than the switch valve 76 may be used selectively to couple the vacuum source or the irrigation source to the bandage. Simple tube clamps, for example, may be used selectively to open and close the tube set provided with bandage 10. When valve 76 is switched to operate the vacuum source 12, the vacuum suction draws exudate up through the holes 74 and radially inwardly through passageways 72 toward port 60 and finally through tube 34.

Vacuum/irrigation tube 34 extends over the edge of packing 30 and out from under the edge of the sealing film 40. In use, irrigation source 14 delivers liquid through tube 34 and port 60 of cover 24 and into passageways 72 of member 19. The fluid moves radially out through passageways 72 to holes 74. The fluid then moves down through holes 74 to impinge on wound surface 18.

Figure 3:
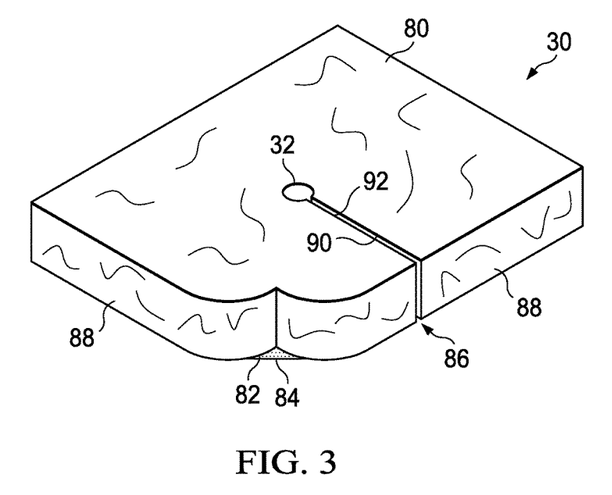
FIG. 3 is a perspective view of the foam packing of the bandage showing then packing having a central aperture and a slit in communication with the aperture and further showing the packing having an adhesive bottom surface for coupling with a top surface of the cover.

As described above, bandage 10 includes foam packing 30. Foam packing includes a top surface 80 and a bottom surface 82. Illustratively, foam packing 30 is rectangular and sized to match member 19. An adhesive 84 may be attached to bottom surface 82, as shown in FIG. 3. In some embodiments, a silicone-based adhesive is provided on bottom surface 82. Packing 30 may be permanently or temporarily affixed to top surface 80 of member 19 to act as a cavity filler for bandage 10. For example, chronic wounds, such as wound 16, often create a deep cavity. Foam packing 30 is added on top of member 19 to essentially fill the cavity created by the wound. In those embodiments in which packing 30 is temporarily attached to or placed on member 19, packing 30 can be removed and replaced by a caregiver without the need to replace member 19.

As mentioned above, packing 30 includes aperture 32 which extends from top surface 80 to bottom surface 82. Illustratively, aperture 32 is centrally located to receive connecter 26 which is centrally located on cover 24 of member 19. It is within the scope of this disclosure for packing 30 to have an aperture which is not centrally located provided that the aperture cooperates with either a connecter of member 19 or with a port of the cover of member 19. As shown in FIG. 4, connecter 26 is received within aperture 32 of packing 30. A portion of vacuum tube 34 is also received within aperture 32 and couples with connecter 26.

As shown in FIGS. 2 and 3, packing 30 further includes a slit 86. Slit 86 is defined by first and second confronting interior surfaces 90, 92 which each extend from top surface 80 to bottom surface 82 and are each in communication with aperture 32. Surfaces 90, 92 each further extend from aperture 32 to a side wall 88, as shown in FIGS. 2 and 3. Slit 86 provides an entryway for tube 34. Slit 86 allows packing 30 to be easily removed and replaced from bandage 10 without the need to disconnect tube 34 from connecter 26 or port 60. When removing packing 30 from member 19, tube 34 is slid through slit 86 from aperture 32 to side wall 88. When placing a new packing 30 on member 19, tube 34 is slid through slit 86 from side wall 88 to aperture 32 to rest one end of tube 34 within aperture 32. Because packing 30 is replaceable separately from member 19, member 19 is able to stay in place on wound surface 18 for a longer period of time.

Figure 5:
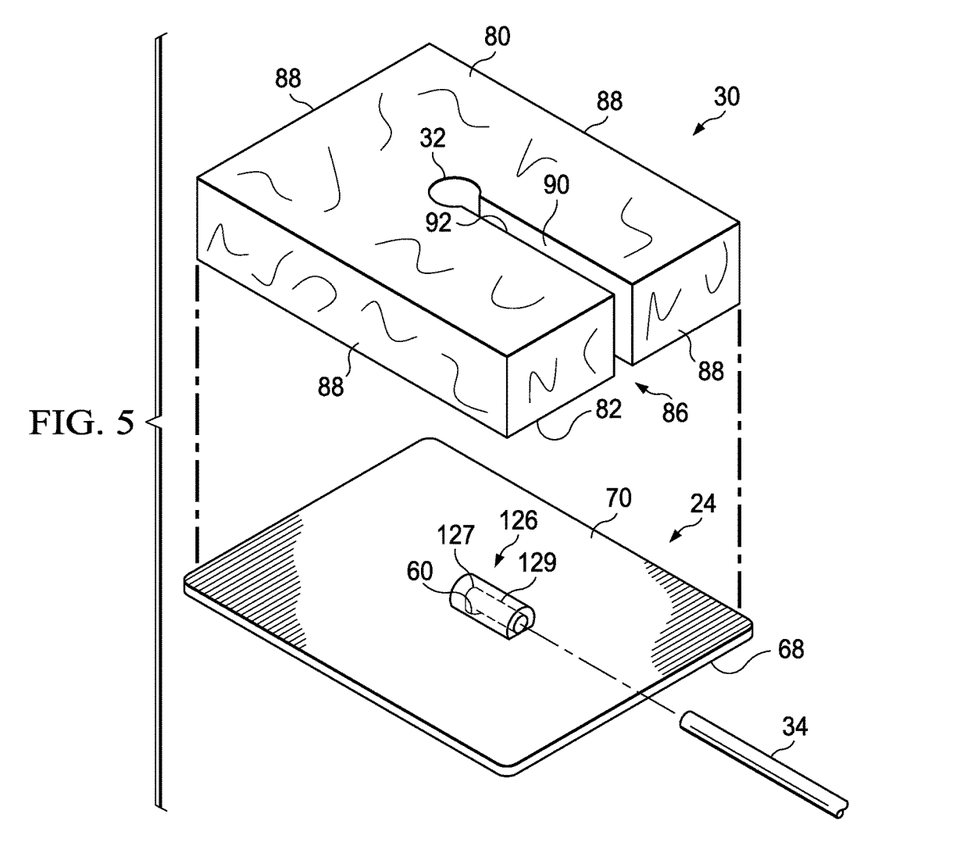
FIG. 5 is a perspective view showing the foam packing of the bandage, the cover of the member, and a horizontal connecter of the member coupled to the member to be received within the aperture of the foam packing.
Figure 6:
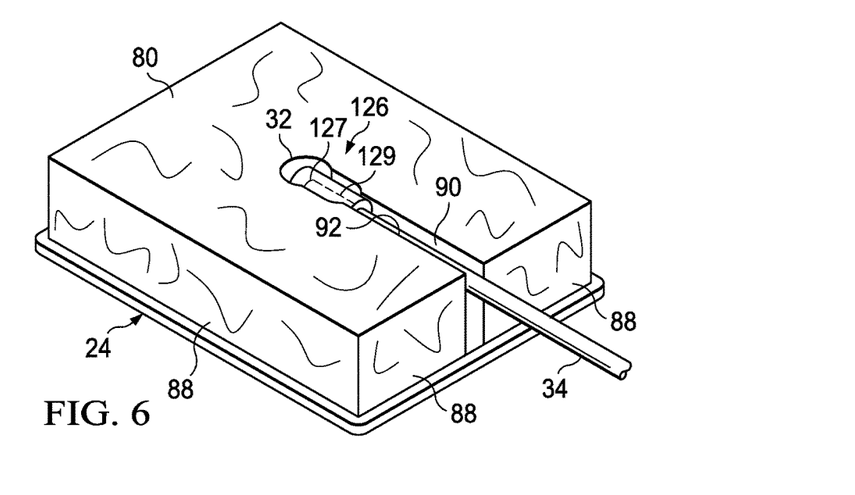
FIG. 6 is a perspective view showing the foam packing adjacent to the bandage and further showing the horizontal connecter of the member received within the aperture of the packing and showing the vacuum tube coupled to the connecter and received within the slit of the packing.

In an alternative embodiment shown in FIGS. 5 and 6, a horizontal connecter 126 is coupled to cover 24. Horizontal connecter 126 includes a vertical passageway 127 connected to a horizontal passageway 129. Horizontal connecter 126 provides for a horizontal attachment for vacuum tube 34, rather than the vertical attachment shown in FIGS. 2 and 4. Horizontal connecter 126 is coupled to cover 24 in the same manner as connecter 26 and communicates with port 60 of cover 24. When foam packing 30 is coupled to or positioned adjacent to cover 24, as shown in FIG. 6, horizontal member 126 is received within aperture 32 of packing 30. Further, tube 34 is received wholly or partially within slit 86 of packing when tube 34 is coupled to connecter 126.

It is within the scope of this disclosure for foam packing 30 to be perforated to facilitate customizing the size of the foam to the wound cavity without using scissors. Further, foam packing 30 includes open-cell or closed-cell types of foam. For example, it is within the scope of this disclosure to include foam packing 30 made of hydrophobic or hydrophilic polyurethane foam or polyvinylalcohol foam.

As mentioned above, bandage 10 includes sealing layer or film 40 that is placed over packing 30 and around tube 34, as shown in FIGS. 2 and 4. Film 40 may be substantially larger than the wound 16 or member 19 and packing 30 to provide an effective seal about the member 19 and the wound 16. Film 40 is provided to cover the entire wound 16 and to extend across and attach around tube 34 to the patient's healthy skin 42, as shown in FIG. 1. Preferably, film 40 is an occlusive or semi-occlusive material which allows water vapor to permeate through. Because of this characteristic, film 40 is referred to as Moisture Vapor Transmission Rate film or MVTR film. The products TEGADERM® brand sealing film made by 3M Corporation and OPSITE FLEXIGRID® made by Smith & Nephew can be used for film 40, for example. The product OPSITE FLEXIGRID® is a semi-permeable film. Film 40 is approximately 0.003 inch (0.076 mm) thick, however, it is within the scope of this disclosure to include an occlusive or semi-occlusive film 40 having other thickness. Film 40 is provided to create a sealed environment below the film 40 and around the wound 16 in which a vacuum or negative pressure can be maintained as provided by vacuum source 12.

Although this invention has been described in detail with reference to certain embodiments variations and modifications exist within the scope and spirit of the invention as described and defined in the following claims.

The invention claimed is:

1. A system for providing vacuum therapy to a tissue site, the system configured for fluid communication with a vacuum source to provide reduced pressure to the tissue site, the system comprising;
   a pack configured to provide at least a portion of a route of fluid communication between the vacuum source and the tissue site, and having an adhesive on a lower surface of the pack;
   a member having a plurality of holes fluidly coupled to the pack and configured to define a plurality of fluid pathways for providing at least a portion of the route of fluid communication between the vacuum source and the tissue site; and
   a sealing layer disposed adjacent the pack and over the member to provide a sealed environment over the tissue site.

2. The system of claim 1, wherein the member includes a plurality of protrusions extending away from the member toward the tissue site.

3. The system of claim 2, wherein the plurality of protrusions comprise a plurality of bosses.

4. The system of claim 2, wherein the plurality of protrusions collectively define at least a portion of the plurality of fluid pathways.

5. The system of claim 1, wherein the member is flexible.

6. A system for providing vacuum therapy to a tissue site, the system configured for fluid communication with a vacuum source to provide reduced pressure to the tissue site, the system comprising;
   a pack configured to provide at least a portion of a route of fluid communication between the vacuum source and the tissue site, and having an adhesive on a lower surface of the pack;
   a member having a plurality of holes fluidly coupled to the pack and configured to define a plurality of fluid pathways for providing at least a portion of the route of fluid communication between the vacuum source and the tissue site, wherein the member includes a plurality of protrusions extending away from the member toward the tissue site.

7. The system of claim 6, wherein the plurality of protrusions comprise a plurality of bosses.

8. The system of claim 6, wherein the plurality of protrusions collectively define at least a portion of the plurality of fluid pathways.

9. The system of claim 6, wherein the member is flexible.

* * * * *